(12) United States Patent
Moore (10) Patent No.: US 11,857,175 B2
(45) Date of Patent: Jan. 2, 2024

(54) VECTOR FIXATION DEVICE

(71) Applicant: Dauntless Innovations, LLC, Germantown, TN (US)

(72) Inventor: Jesse Moore, Frisco, TX (US)

(73) Assignee: DAUNTLESS INNOVATIONS, LLC, Germantown, TN (US)

( * ) Notice: Subject to any disclaimer, the term of this patent is extended or adjusted under 35 U.S.C. 154(b) by 811 days.

(21) Appl. No.: 16/787,974

(22) Filed: Feb. 11, 2020

(65) Prior Publication Data

US 2020/0170636 A1 Jun. 4, 2020

Related U.S. Application Data

(63) Continuation of application No. 15/208,351, filed on Jul. 12, 2016, now abandoned, which is a continuation of application No. 14/305,408, filed on Jun. 16, 2014, now abandoned.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01); *A61B 2017/044* (2013.01); *A61B 2017/0445* (2013.01); *A61B 2017/0453* (2013.01); *A61B 2017/0458* (2013.01); *A61B 2017/0496* (2013.01); *A61F 2002/0829* (2013.01); *A61F 2002/0852* (2013.01); *A61F 2002/0882* (2013.01)

(58) Field of Classification Search
CPC ........ A61B 17/0401; A61B 2017/0404; A61B 2017/044; A61B 2017/0445; A61B 2017/0453; A61B 2017/0458; A61B 2017/0496; A61F 2/0811; A61F 2002/0829; A61F 2002/0852; A61F 2002/0882

See application file for complete search history.

(56) References Cited

U.S. PATENT DOCUMENTS

| | | |
|---|---|---|
| 5,306,290 A | 4/1994 | Martins et al. |
| 5,474,554 A | 12/1995 | Ku |
| 5,571,139 A | 11/1996 | Jenkins, Jr. |

(Continued)

OTHER PUBLICATIONS

Bryant et al., Comparison of cannulated screws with FiberWire or stainless steel wire for patella fracture fixation: A pilot study, Journal of Orthopaedics, vol. 12, No. 2, Jun. 2014, pp. 92-96, Elsevier India Pvt. Ltd.

(Continued)

*Primary Examiner* — Yashita Sharma (57) ABSTRACT

A fixation apparatus is provided that includes a reception portion on a proximal end of the fixation apparatus. The reception portion couples the fixation apparatus to a tension element, and adjustment of the tension element with respect to the fixation apparatus does not cause a change in a position of the fixation apparatus. The fixation apparatus also includes a chamber in a distal portion of the fixation device. The chamber provides a supportive enclosure for a tension element that runs through the chamber and is anchored at the reception portion, and a force vector of the tension element exiting at the distal end of the fixation device is redirected at an axis independent of the axis of the fixation apparatus from the proximal end to the distal end.

18 Claims, 7 Drawing Sheets

(56) References Cited

U.S. PATENT DOCUMENTS

| | | |
|---|---|---|
| 5,571,184 A | 11/1996 | DeSatnick |
| 5,702,397 A | 12/1997 | Goble et al. |
| 6,099,568 A | 8/2000 | Simonian et al. |
| 6,117,160 A | 9/2000 | Bonutti |
| 6,171,310 B1 | 1/2001 | Giordano et al. |
| 6,368,326 B1 | 4/2002 | Dakin et al. |
| 6,589,245 B1 | 7/2003 | Weiler et al. |
| 6,629,977 B1 | 10/2003 | Wolf |
| 6,994,725 B1 | 2/2006 | Goble |
| 7,172,595 B1 | 2/2007 | Goble |
| 7,410,489 B2 | 8/2008 | Dakin et al. |
| 7,572,275 B2 | 8/2009 | Fallin et al. |
| 7,585,311 B2 | 9/2009 | Green et al. |
| 7,591,823 B2 | 9/2009 | Tipirneni |
| 7,828,820 B2 | 11/2010 | Stone et al. |
| 7,837,717 B2 | 11/2010 | Deffenbaugh et al. |
| 8,062,295 B2 | 11/2011 | McDevitt et al. |
| 8,147,514 B2 | 4/2012 | Bonutti |
| 8,267,964 B2 | 9/2012 | Green et al. |
| 8,282,674 B2 | 10/2012 | Gelfand |
| 9,131,937 B2 | 9/2015 | Chan et al. |
| 9,259,217 B2 | 2/2016 | Fritzinger et al. |
| 2006/0241694 A1 | 10/2006 | Cerundolo |
| 2008/0288070 A1 | 11/2008 | Lo |
| 2009/0036929 A1 | 2/2009 | Reglos et al. |
| 2009/0234451 A1 | 9/2009 | Manderson |
| 2009/0312794 A1 | 12/2009 | Nason et al. |
| 2010/0262185 A1 | 10/2010 | Gelfand et al. |
| 2012/0130492 A1 | 5/2012 | Eggli et al. |
| 2013/0123841 A1 | 5/2013 | Lyon |
| 2013/0172944 A1 | 7/2013 | Fritzinger et al. |
| 2013/0289574 A1 | 10/2013 | Shinde |
| 2013/0331897 A1 | 12/2013 | Holt |
| 2016/0089131 A1 | 3/2016 | Wade |

OTHER PUBLICATIONS

Mayurasakorn et al., Cannulated Screws and Braided Polyester Tension Band as an Alternative for Fixation of Transverse Patella Fracture: A Finite Element Analysis Study, The Bangkok Medical Journal, vol. 13, No. 2, Sep. 2017, pp. 11-18, Bangkok Dusit Medical Services, Plc., Bangkok, Thailand.

Ono et al., Knotless anchors with sutures external to the anchor body may be at risk for suture cutting through osteopenic bone, Bone & Joint Research, vol. 5, No. 6, Jun. 2016, pp. 269-275, The British Editorial Society of Bone & Joint Surgery, London.

St-Jean et al., Braided tape suture provides superior bone pull-through strength than wire suture in greater tuberosity of the humerus, Journal of Orthopaedics, vol. 12, Supplemental No. 1, Feb. 2015, pp. S14-S17, Reed Elsevier India Pvt. Ltd.

Swanson, et al., "A Minimally Invasive Surgical Technique to Treat Distal Clavicle Fractures", Orthopedics, Jul. 2009, 5 pages, vol. 32 Issue 7, Healio.com (online publication), USA.

VECTOR FIXATION DEVICE

CROSS-REFERENCE TO RELATED APPLICATION

This application is a continuation application of and claims priority from U.S. patent application Ser. No. 15/208,351, filed Jul. 12, 2016, which is a continuation application of and claims priority from U.S. patent application Ser. No. 14/305,408, filed on Jun. 16, 2014, the entirety of which is incorporated herein by reference.

BACKGROUND OF THE INVENTION

Field of the Invention

The field of the invention is medical devices, and more specifically bone and tissue fixation devices.

Description of Related Art

Bones provide a rigid structure for the human body and provide support and protection for various organs. Occasionally, a bone, or other organic tissue, may become fractured. In some cases, surgical methods are used to treat fractured bones, in order to stabilize the bone so that the fracture heals properly.

In some instances, orthopedic surgery requires the use of implants to support orthopedic reconstruction. For example, it may be necessary to insert bone screws, plates, pins, rods, wires, interlocking nails, or other devices to support the bone, or other tissue, while healing.

SUMMARY OF THE INVENTION

A fixation apparatus is provided that includes a reception portion on a proximal end of the fixation apparatus. The reception portion couples the fixation apparatus to a tension element, and adjustment of the tension element with respect to the fixation apparatus does not cause a change in a position of the fixation apparatus. The fixation apparatus also includes a chamber in a distal portion of the fixation device. The chamber provides a supportive enclosure for a tension element that runs through the chamber and is anchored at the reception portion, and a force vector of the tension element exiting at the distal end of the fixation device is redirected at an axis independent of the axis of the fixation apparatus from the proximal end to the distal end.

A method is provided for fractured bone repair. The method includes inserting a fixation device into a first segment of organic tissue along a central axis of the fixation device. The method also includes threading a tension element through a chamber portion of the fixation device. The method also includes anchoring, at a proximal end of the fixation device, the tension element to a button, wherein the fixation device comprises a button reception portion that couples the button to the fixation device. The method also includes attaching the tension element to an anchor in a second segment of organic tissue such that a force vector of the tension element at the distal end of the fixation device is redirected at an axis independent of the axis of the fixation apparatus from the proximal end to the distal end.

A fixation apparatus is provided. The fixation apparatus includes a chamber through a fixation device. The chamber provides a supportive enclosure for a tension element that runs through the chamber and couples to the fixation device at a proximal end of the fixation device, and a force vector of the tension element at the distal end of the fixation device is redirected at an axis independent of the axis of the fixation apparatus from the proximal end to the distal end. The fixation apparatus also includes a tissue engagement portion of the fixation device. An outside surface of the tissue engagement portion includes anti-migration elements to secure the apparatus in the position in organic tissue, and a force exerted on the tension element is redirected to secure anatomy. Adjustment of the tension element with respect to the fixation device does not cause a change in a position of the fixation device.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION OF EXEMPLARY EMBODIMENTS

Exemplary methods, apparatus, and products for a vector fixation device in accordance with the present invention are described with reference to the accompanying drawings, beginning with FIG. 1. In one or more embodiments, the present invention is directed to a vector fixation device that provides a supportive enclosure for a tension element that extends outside the vector fixation device poly-axially.

Figure 1:
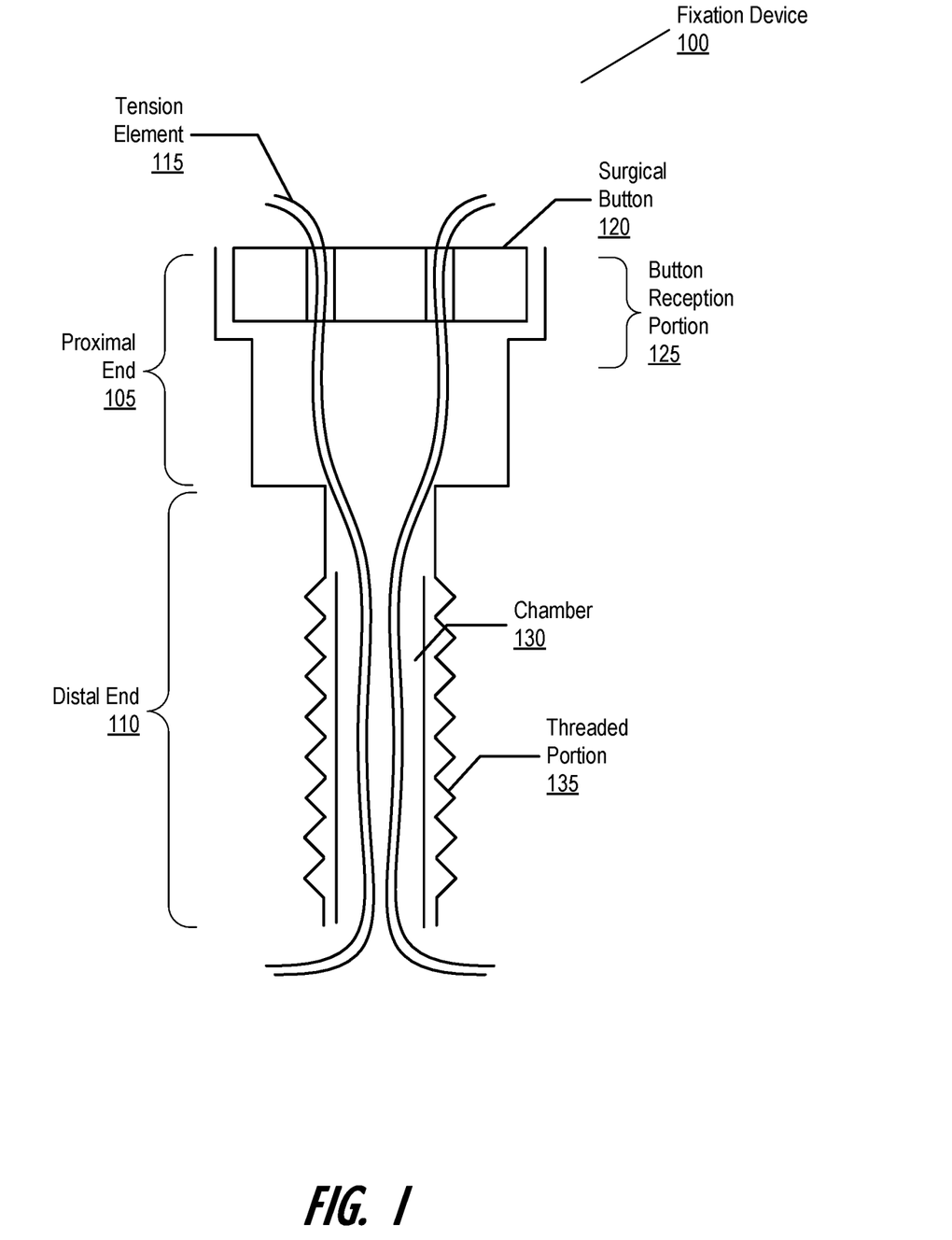
FIG. 1 sets forth a line drawing illustrating a cross section view of an example fixation device for fractured bone or tissue repair, according to one or more embodiments.

FIG. 1 sets forth a cross section view of a fixation device (100), or fixation apparatus, for fractured bone or tissue repair, according to one or more embodiments. Fixation device (100) may be a cannulated bone screw, vector screw, vector anchor, or any similar cannulated member that is used to reinforce the fixation within bone or other organic tissue in a body. In one or more embodiments, fixation device (100) may include a drive feature used to insert the fixation device (100) into organic tissue, such as bone, which will be described in more detail with respect to FIGS. 2-3. In one or more embodiments, fixation device (100) includes a threaded portion (135), such as helical ridges on an outside surface of fixation device (100) that facilitates entry into the tissue using a screw motion. In one or more embodiments, the threaded portion (135) may encompass the entire surface of the fixation device (100). The threaded portion (135) may also be a tissue engagement portion, and fixation device (100) may include other non-helical ridges to prevent migration of fixation device (100) once it is inserted into bone or other tissue. For example, fixation device (100) may include anti-migration elements on an outside surface, including ribs or grooves on the outside surface or a porous mesh on the outside surface of the fixation apparatus for a tissue ingrowth portion to affix the fixation apparatus in position in organic tissue.

Fixation device (100) includes a proximal end (105) and a distal end (110). Proximal end (105) includes a reception portion (125) within which a surgical button (120) or other anchor may be loosely or rigidly attached to the fixation device (100). For example, in one or more embodiments, the anchor may be simply a tension element that has been knotted such that it is anchored at the proximal end (105) without the use of a surgical button.

According to one or more embodiments, the surgical button (120) may sit within the reception portion (125). In one or more embodiments, surgical button (120) may be a height adjusting button, a free floating button, or a retained button. That is, surgical button (120) may fit over the proximal end (105) of fixation device (100), may sit inside proximal end (10) of fixation device (100), or may float atop proximal end (105) of fixation device (100). Adjustment of the placement of the button with respect to the fixation device allows the button to protrude from the proximal end (105) of the fixation device, to be flush with the proximal end (105) of the fixation device, or to be fully hidden within the proximal end (105) of the fixation device. Adjusting the placement or the button with respect to the fixation device allows the fixation device (100) and button (120) to sit flush, above, or below bone or other organic tissue, and allows the button to be strategically positioned around sensitive anatomy.

In one or more embodiments, either or both of fixation device (100) and surgical button (120) may include features that allow for rigid coupling of the surgical button (120) to the fixation device (100). These features may include, for example, helical threads or other ridges that affix the surgical button to proximal end (15) of fixation device (100), as will be described in further detail with respect to FIG. 4. The position of surgical button (120) may be adjusted with respect to fixation device (100) without causing a change in a position of the fixation device within organic tissue.

Surgical button (120) provides an anchor for tension element (115). However, in one or more embodiments, tension element (115) may be anchored without the use of surgical button (120). In one or more embodiments, tension element (115) may be sutures, synthetics, biologic, or a combination of materials, including grafted tissue, and may be secured, for example, using a knot, to surgical button (120), or directly within proximal end (105) without the use or a surgical button (120). Tension element (115) may be used to tighten or hold two or more segments of organic tissue. In one or more embodiments, tension element (115) may be used to tighten or hold a tendon to a bone. For example, tension element (115) may be knotted more tightly at surgical button (120) to cause greater tension in tension element (115).

Tension element (115) passes through fixation device (100) through chamber (130) in the distal end (110), and chamber (130) provides a supportive enclosure for tension element (115). In addition, the proximal end (100) also includes a hollow portion that allows tension element (115) to pass through the entire fixation device (100) from proximal end (105) to distal end (110). Tension element (115) passes through chamber (130) at an axis corresponding to that of the central axis of fixation apparatus (100) from the proximal end (105) to distal end (110).

According to one or more embodiments, tension elements (115) exits fixation device (100) at the distal end (110) at an axis independent of the axis of the fixation apparatus from the proximal end (105) to the distal end (110). Said another way, tension element (110) redirects a force vector of the tension element (115) poly-axially at the distal end (110). As will be described with respect to FIGS. 6-7, in one or more embodiments, tension element (115) may pass through chamber (130) and anchor to one or more additional anchors, surgical buttons, or fixation devices independent from fixation device (100), within a same organic tissue segment, or across multiple tissue segments.

Figure 2:
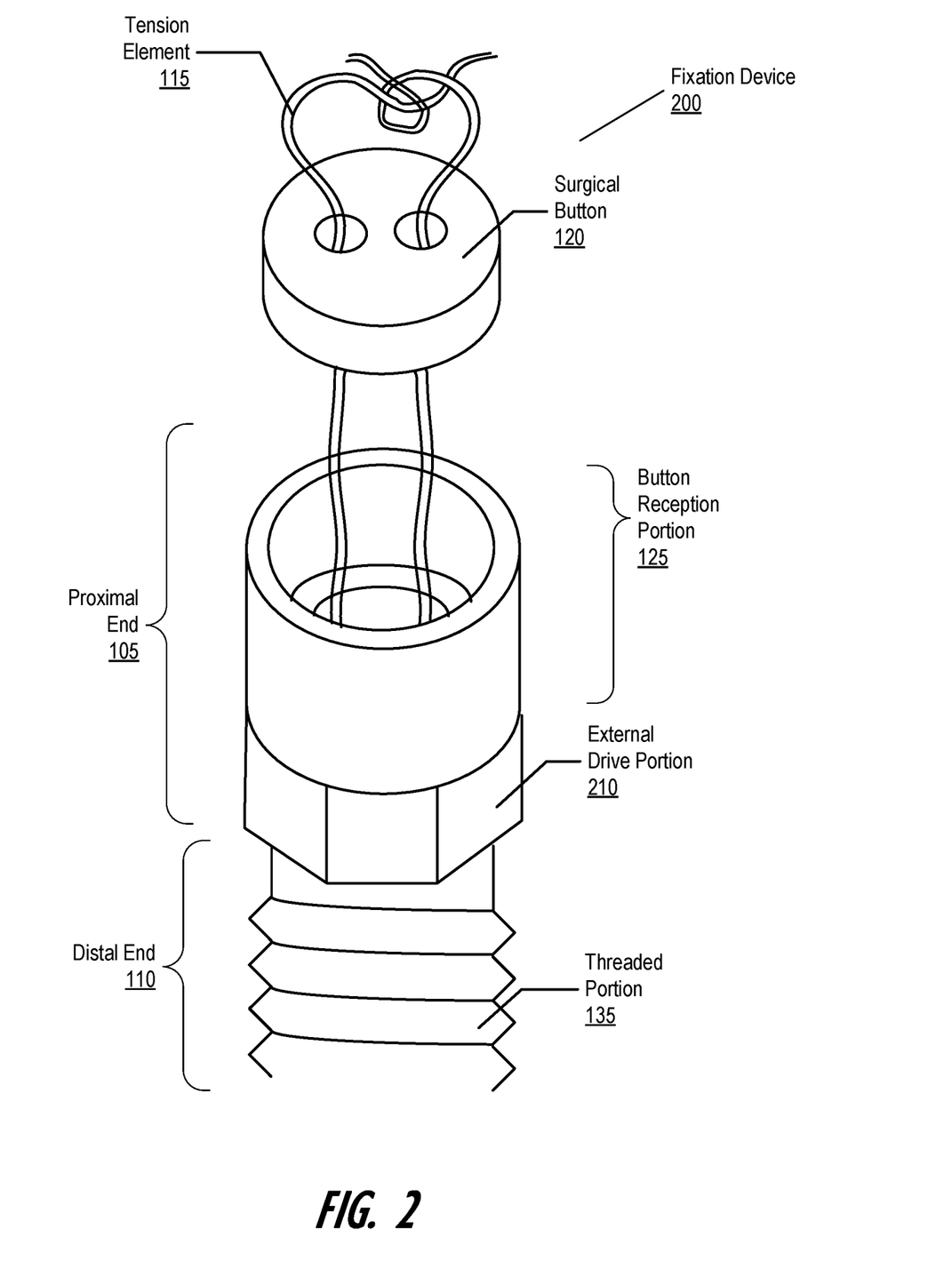
FIG. 2 sets forth a line drawing illustrating an example fixation device fixation device for fractured bone or tissue repair utilizing an external drive portion, according to one or more embodiments.

FIG. 2 sets forth a diagram of an example fixation device (200) for fractured bone or tissue repair utilizing an external drive portion, according to one or more embodiments. As in FIG. 1, fixation device (200) includes a proximal end (105) and distal end (110). Surgical button (120) sits inside button reception portion (125) of fixation device (200). Fixation device (200) also includes a chamber that acts as a supportive enclosure for tension element (115), which is anchored at surgical button (120). Fixation device (200) also depicts external drive portion (210), which provides a surface for a user to apply a force such that the helical ridges in threaded portion (135) drives fixation device (200) into organic tissue, such as bone. In one or more embodiments, the threaded portion (135) acts as an anti-migration element, to affix the fixation device (300) in position in organic tissue.

Figure 3:
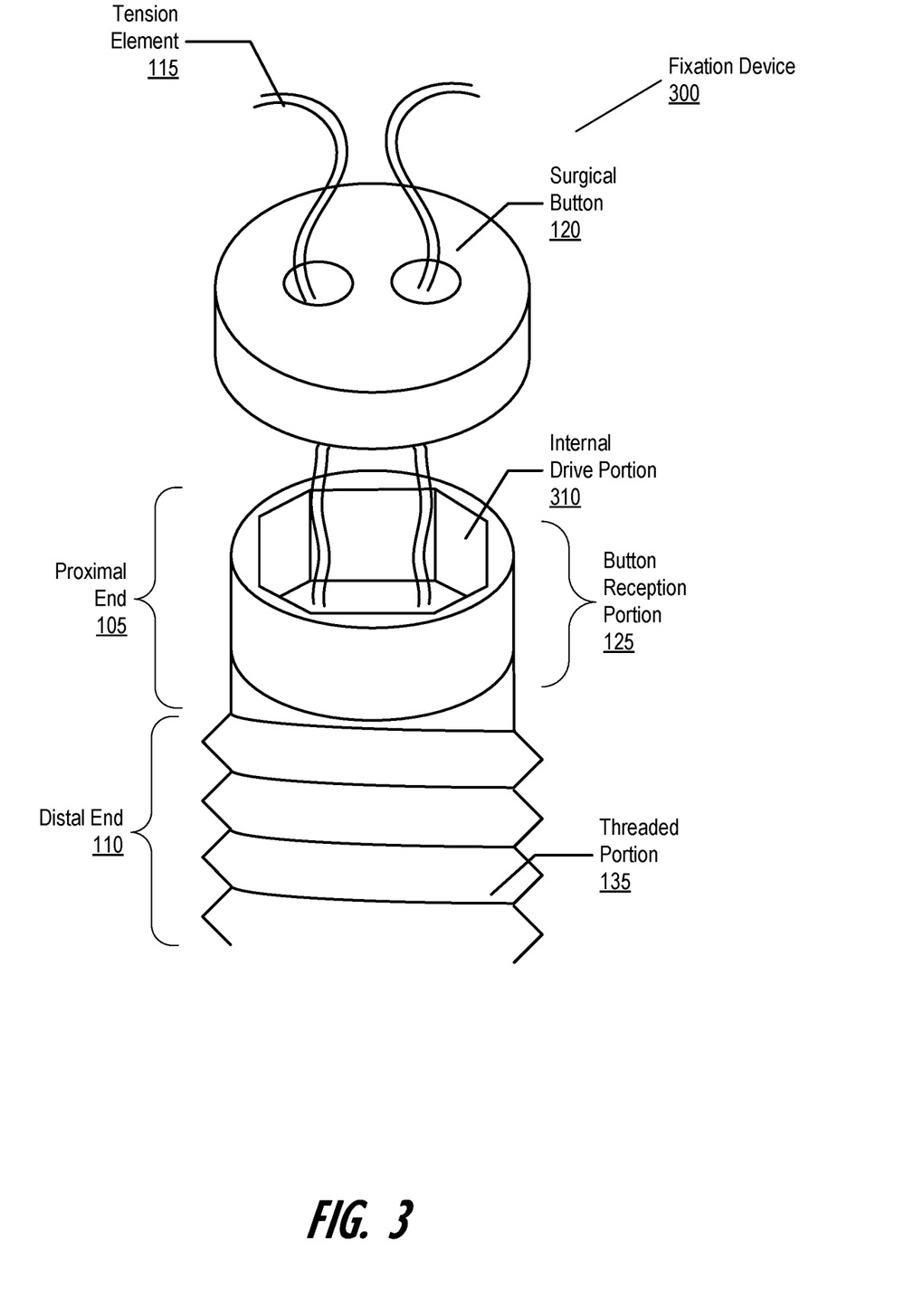
FIG. 3 sets forth a line drawing illustrating an example fixation device for fractured bone or tissue repair utilizing an internal drive portion, according to one or more embodiments.

FIG. 3 sets forth a diagram of an example fixation device for fractured bone or tissue repair utilizing an internal drive portion, according to one or more embodiments. As in FIG. 1, fixation device (300) includes a proximal end (105) and distal end (110). Surgical button (120) sits inside button reception portion (125) of fixation device (300). Fixation device (300) also includes a chamber that acts as a supportive enclosure for tension element (115), which is anchored at surgical button (120). Fixation device (300) also depicts internal drive portion (310), which provides a surface for a user to apply a force such that the helical ridges in threaded portion (135) drives fixation device (300) into organic tissue, such as bone. In one or more embodiments, the threaded portion (135) acts as an anti-migration element, to affix the fixation device (300) in position in organic tissue.

Figure 4:
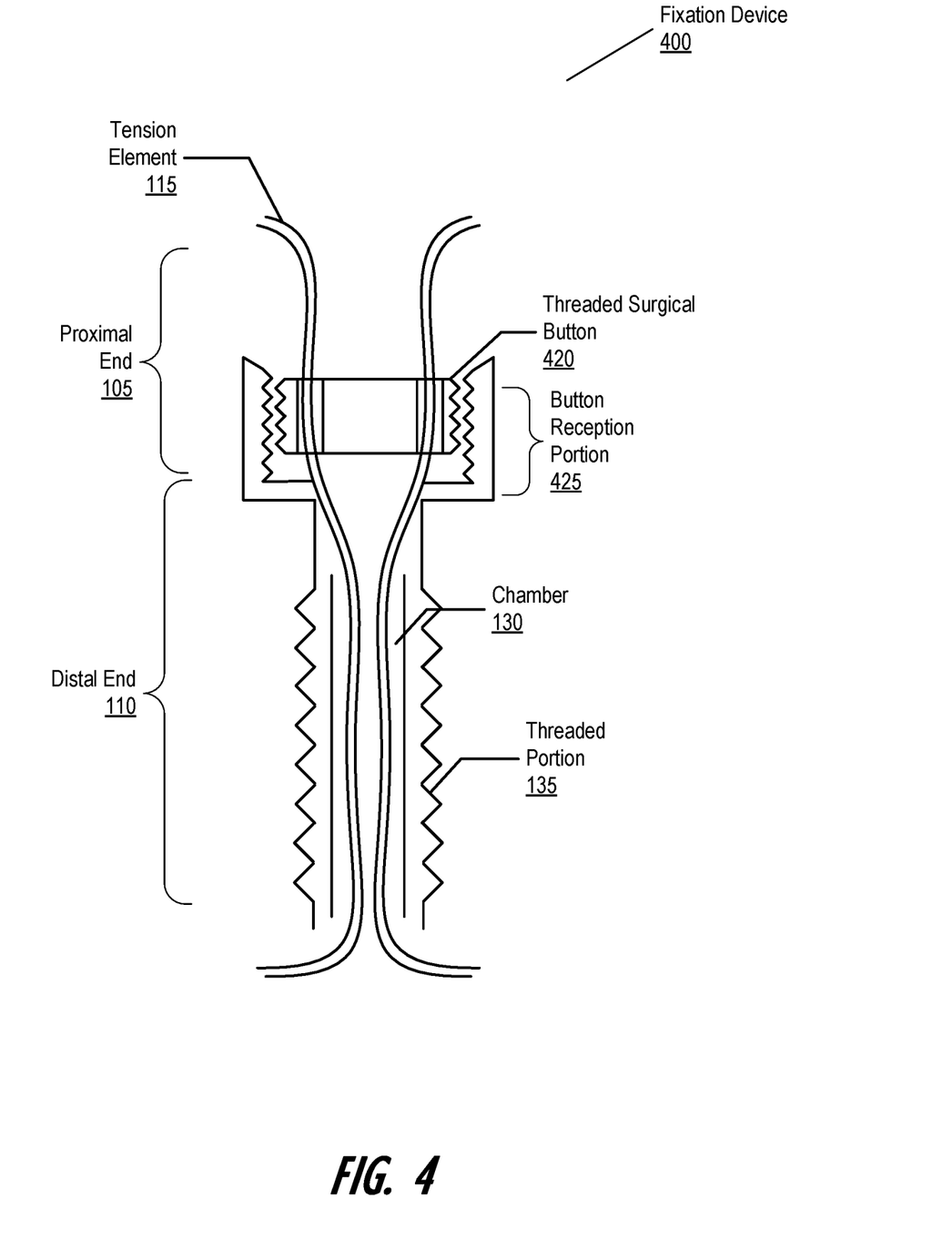
FIG. 4 sets forth a line drawing illustrating a cross section view of an example fixation device for fractured bone or tissue repair utilizing a threaded button, according to one or more embodiments.

FIG. 4 sets forth a cross section view of a fixation device for fractured bone or tissue repair utilizing a threaded button, according to one or more embodiments. As in FIG. 1, fixation device (400) includes a proximal end (105) and distal end (110). Tension element (115) is also threaded through chamber (130), and threaded portion (135) includes helical ridges on an outside surface of fixation device (100) that facilitates entry into the tissue.

Fixation device (400) additionally includes threaded surgical button (420) that is affixed inside button reception portion (425) of fixation device (400) using helical ridges, or threads, inside button reception portion (425). In one or more embodiments, threaded surgical button (420) may include other characteristics, such as non-helical ridges, that allow threaded surgical button (420) to loosely but securely couple to fixation device (400) within button reception portion (425). Thus, the position of surgical button (420) may be adjusted with respect to fixation device (400)

without causing a change in position of the fixation device (400) within the organic tissue.

For example, in one or more embodiments, threaded surgical button (420) may be screwed, or otherwise adjusted, in or out of button reception portion (425) to adjust the height of the button with respect to fixation device (400). Adjusting the position of the threaded surgical button (420), or any button (i.e., surgical button 120), causes a change in the tension in tension element (115) without adjusting the position of fixation device (400). The button may be rest above, within, or partially extended from the proximal end of fixation device and strategically positioned around sensitive anatomy. In one or more embodiments, threaded surgical button (420) may be adjusted to modify the tension of tension element (115) to hold a segment of organic tissue to another segment of organic tissue, or tendon to a bone for healing. For example, increasing the height of threaded surgical button (420) will cause an increased tension in tension element (115) when tension element (115) is anchored at threaded surgical button (420).

Figure 5:
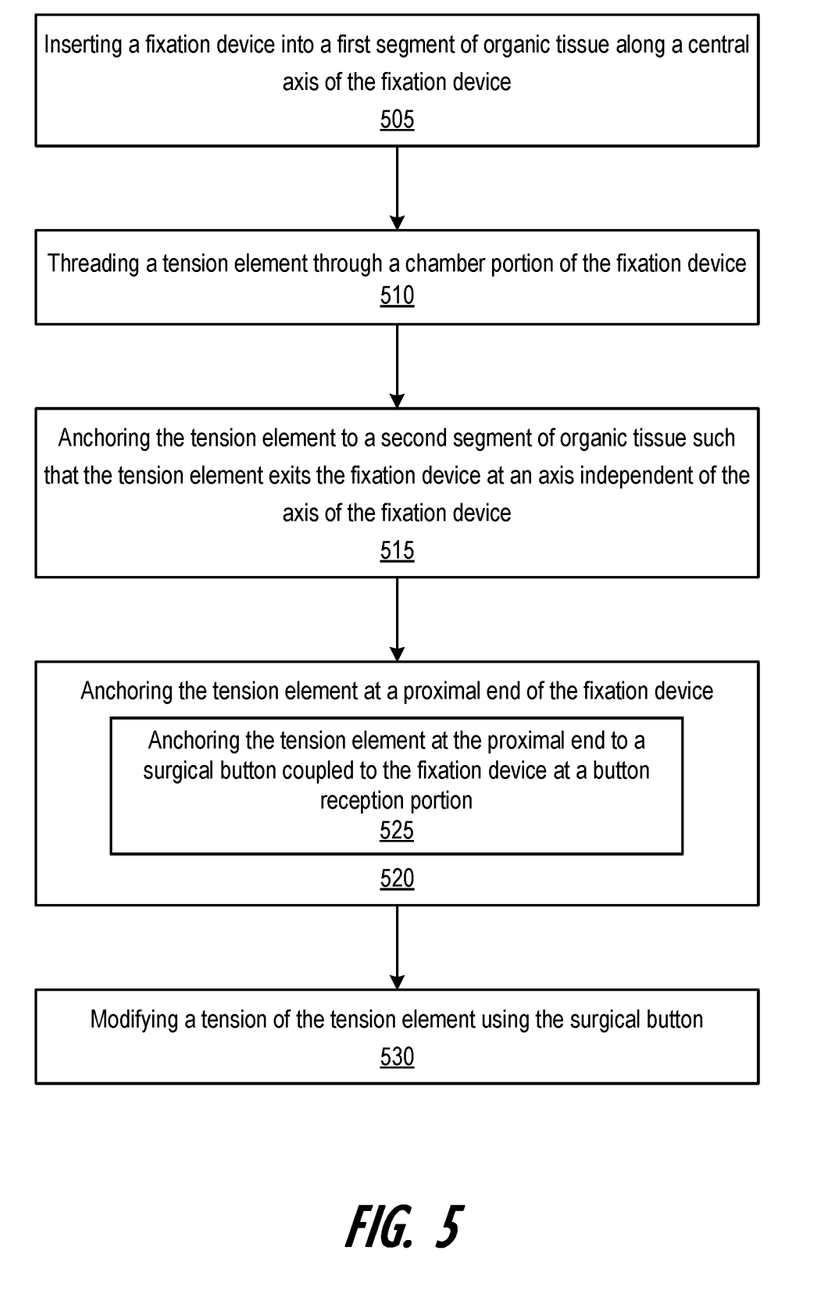
FIG. 5 sets forth a flow chart illustrating an example method for utilizing a fixation device, according to one or more embodiments.

FIG. 5 sets forth a flow chart illustrating an example method for utilizing a fixation device, according to one or more embodiments. While the steps provided are listed in a linear order, according to one or more embodiments, any or all of the steps may occur in a different order, or simultaneously. In addition, in one or more embodiments, one or more of the steps may be omitted. In the example method of FIG. 5, reference may be made to the example fixation devices with reference to FIGS. 1-4.

The example method of FIG. 5 includes inserting (505) a fixation device (100) into a first segment of organic tissue along a central axis of the fixation device (100). In one or more embodiments, the fixation device is inserted by applying a force to the drive portion (210, 310), to cause the fixation device (100) to enter organic tissue. In one or more embodiments, the fixation device may be affixed into organic tissue using anti-migration elements on a threaded portion, or tissue engagement portion, such as the helical ridges, non-helical ridges, ribs, grooves, porous mesh, or any other feature on an external portion of the fixation device that affixes the fixation device into position in organic tissue. The fixation device (100) is placed into a proximal bone or other tissue segment at an appropriate depth.

The example method also includes threading (510) a tension element (115) through a chamber portion (130) of the fixation device (100). In one or more embodiments, the fixation device (100) is inserted prior to inserting the fixation device (100) into the organic tissue by drilling a primary tunnel to allow passage of the tension element (115), as well as a toggle to guide the tension element. The toggle is loaded with the tension element (115) and passed through the tunnel. Then the fixation device (100) is loaded over the tension element (115) with the tension element running through the chamber (130). The tension element (115) is threaded through the chamber (13) in fixation device (100) such that the tension element (115) is independent from the fixation device (100).

The example method also includes anchoring (515) the tension element to a second segment of organic tissue such that the tension element exist the fixation device (100) at an axis different than the axis of the fixation device. In one or more embodiments, the anchor is a second surgical button that is placed in the second segment of organic tissue either with or without a second fixation device or surgical button. The second segment of organic tissue may be an independent segment or organic tissue, or merely a second portion of one organic tissue. In one or more embodiments, the tension element is attached to the anchor by drilling a second tunnel in the second segment of organic tissue. The tension element (115) may be intercepted from the primary tunnel and pulled through the secondary tunnel to attach to the second anchor. In one or more embodiments, the tension element may be placed to hold a tendon to a bone for healing. Further, in one or more embodiments, multiple other fixation devices may be used in conjunction.

The example method also includes anchoring (520) the tension element (115) at a proximal end (105) of the fixation device (100). The tension element (115) is anchored such that the anchor, such as the knotted tension element or a surgical button, is appropriated below, at, or above the cortical bone edge.

In one or more embodiments, the method includes anchoring (525) the tension element at the proximal end of the fixation device (100) to a surgical button (120) coupled to the fixation device (100) at a button reception portion. Anchoring the tension element may include threading the tension element (115) through the button (120) and securely tightening, for example knotting, tension element (115). The surgical button (120) is coupled, loosely or rigidly, to the fixation device (100) such that adjustment of the surgical button with respect to the fixation device does not cause a change in a position of the fixation device (100).

The example method also includes modifying (530) a tension of the tension element using the surgical button. Adjustment of the surgical button (120) with respect to the fixation device does not cause a change in a position of the fixation device (100). For example, in one or more embodiments, the button reception portion includes threads that couple the surgical button to the fixation device. The height of the surgical button with respect to the fixation device, or the anchor of the tension element at the surgical button, may be adjusted using the threads to modify the tension of the tension element.

Figure 6:
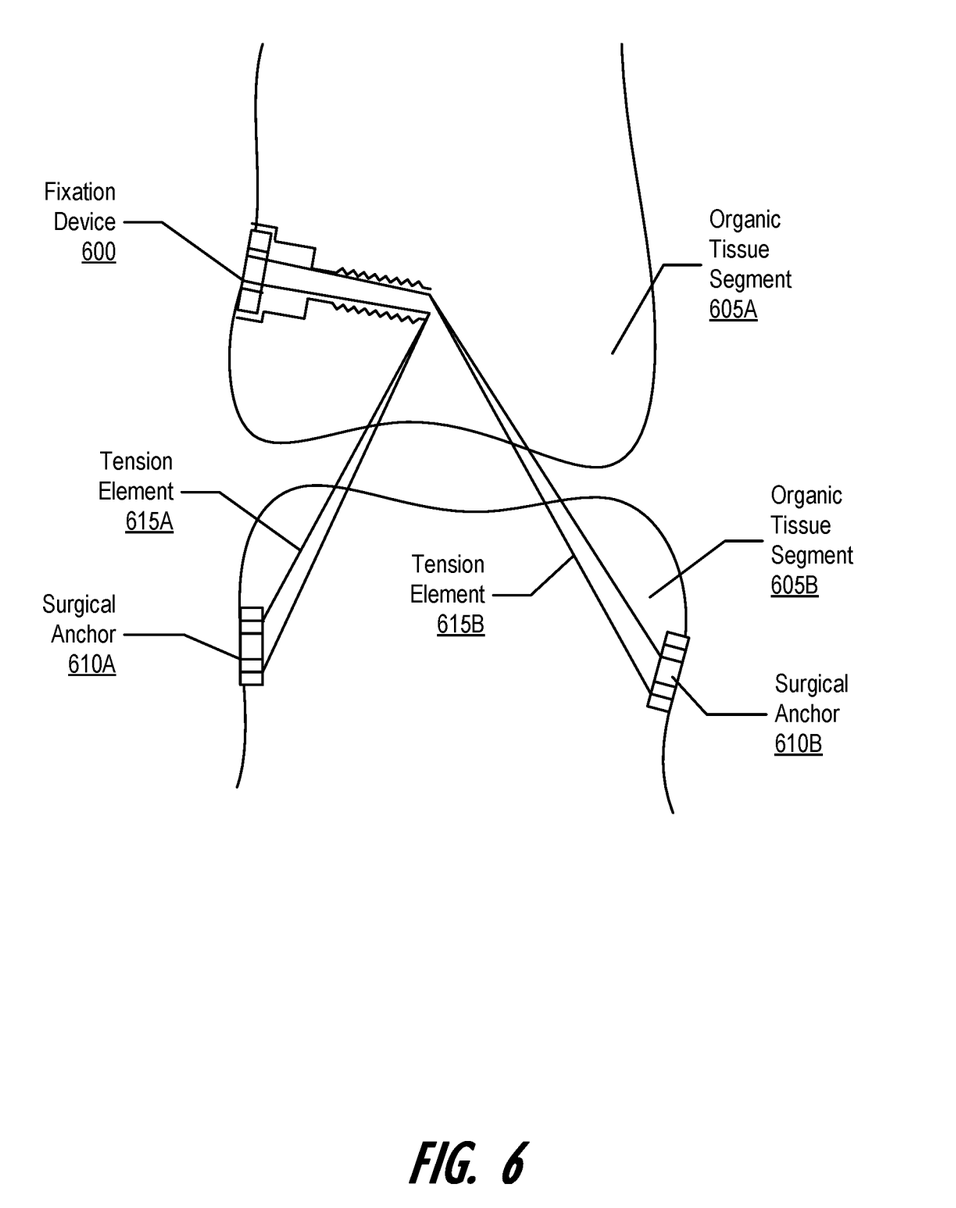
FIG. 6 sets forth a line drawing of a schematic view utilizing a fixation device, according to one or more embodiments.

FIG. 6 discloses a schematic view of utilizing a fixation device, according to one or more embodiments. It will be understood that the following description is merely intended to provide an example of one or more embodiments, and is not intended to limit the various embodiments of the invention.

FIG. 6 includes two organic tissue segments (605A, 605B). Fixation device (600) is inserted into organic tissue segment (605A), and tension elements (615A, 615B) are threaded through fixation device (600). Tension elements (615A, 615B) are anchored to surgical anchors (610A, 610B) in organic tissue segment (605B). In one or more embodiments, surgical anchors (610A, 610B) are surgical buttons, or any other anchor used to anchor a tension element in organic tissue. As depicted, fixation device (600) may be used to connect one or more tension elements to several other anchors or fixation devices.

Tension elements (615A, 615B) follow a central axis of fixation device (600) within the chamber. Upon exiting fixation device (600) at the distal end, tension elements (615A, 615B) run from the distal end of fixation device (600) to each of surgical anchor (610A) and surgical anchor (610B) at angle such that the tension elements (615A, 615B) run from the distal end of fixation device (600) to each surgical anchor (610A, 610B) at a different axis than the central axis of fixation device (600). That is, upon exiting the distal end of fixation device (600), the tension in tension elements (615A, 615B) is redirected at angles towards surgical anchors (610A, 610B), respectively, as the tension elements exit the fixation device poly axially, at an axis independent of the axis of the fixation device.

According to one or more embodiments, the tension in tension elements (615A, 615B) can be adjusted at fixation device (600), for example, by adjusting a surgical button coupled to fixation device (600), as described above. In one or more embodiments, adjusting the tension in tension elements (615A, 615B) causes the organic tissue segments (605A, 605B) to be held together, or in a position suitable for healing.

Figure 7:
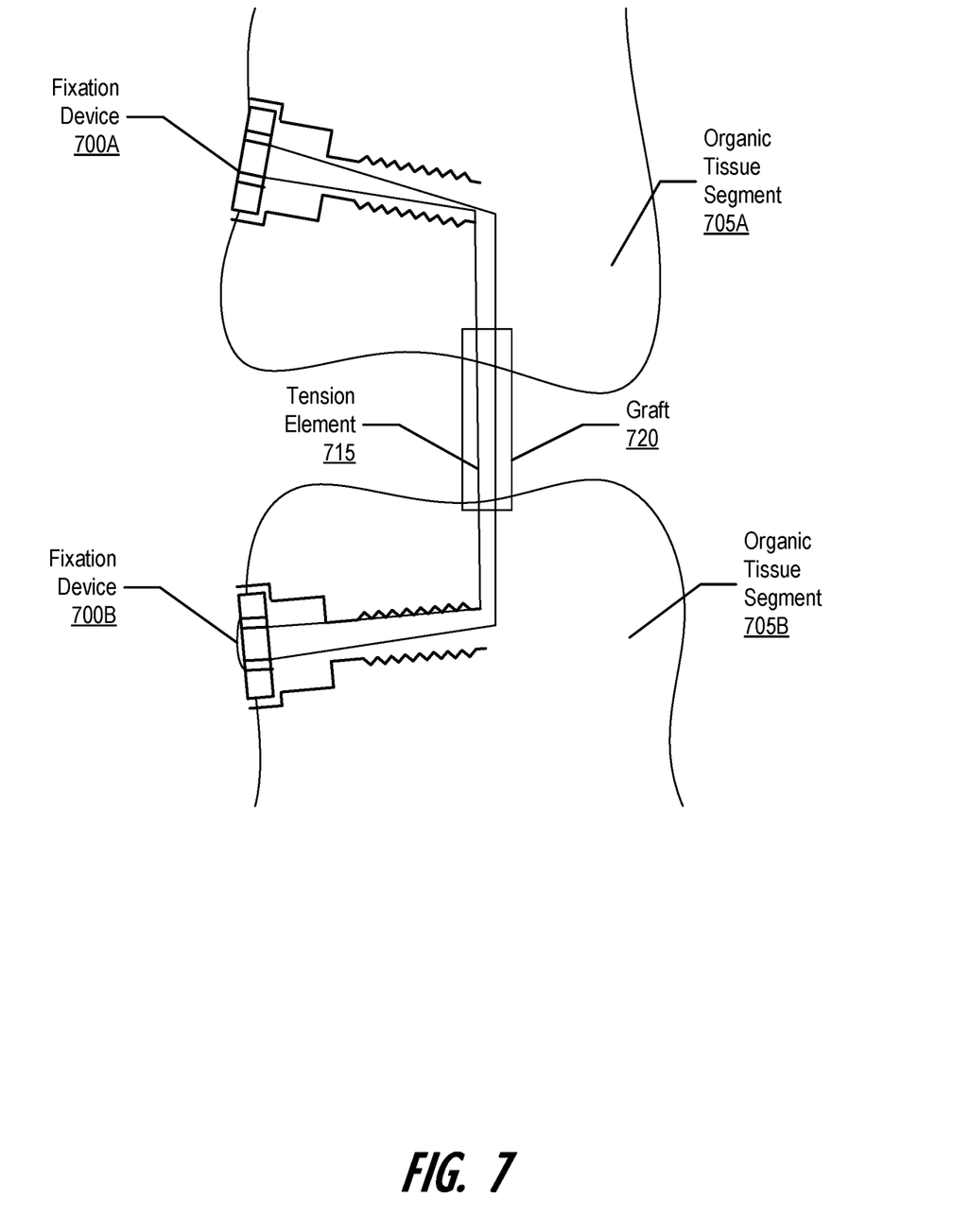
FIG. 7 sets forth a line drawing of a schematic view utilizing multiple fixation devices, according to one or more embodiments.

FIG. 7 discloses a schematic view of utilizing multiple fixation devices, according to one or more embodiments. It will be understood that the following description is merely intended to provide an example of one or more embodiments, and is not intended to limit the various embodiments of the invention.

FIG. 7 includes two organic tissue segments (705A, 705B). Fixation devices (700A, 700B) are inserted into organic tissue segments (705A, 705B), respectively, and tension element (715) is threaded through fixation devices (700A, 700B). Tension element (715) is anchored to surgical buttons or other anchors couple to each of fixation devices (700A, 700B) in organic tissue segments (705A, 705B).

Tension element (715) follows a central axis of fixation device (700A) and a central axis of fixation device (700B) within the chambers of each fixation device. Upon exiting each fixation device at the distal end, tension element (715) runs from the distal end of fixation device (700A) to the distal end of fixation device (700B) at angle such that the tension element (715) runs between fixation device (700A) and fixation device (700B) at a different axis than the central axis of either of fixation device (700A) or fixation device (700B).

According to one or more embodiments, the tension in tension elements (715) can be adjusted at either or both or fixation device (700A) and fixation device (700B), for example, by adjusting a surgical button coupled to fixation device (700A) or fixation device (700B), as described above. In one or more embodiments, adjusting the tension in tension element (715) causes the organic tissue segments (705A, 705B) to be held together, or in a position suitable for healing. In one or more embodiments, additional devices may be used to support tension element (715), such as graft (720).

In view of the explanations set forth above, readers will recognize that the benefits of the vector fixation device according to embodiments of the present invention include utilizing a reinforced fixation within the bone or tissue by means of a cannulated member, such as a cannulated bone screw or other fixation device. The fixation device reinforces a tension element using the fixation device allows for poly axial tension elements. The ability to secure tissue in directions that are not co-axial with the fixation apparatus allows for repair of comminuted fractures, small bones, and complex anatomy. The incorporation of a polyaxial tension element within a fixation apparatus enables surgeons to combine soft tissue repairs and fusion procedures with a singular device that may be more efficient than traditional techniques.

In addition, a more secure docking point than a simple surgical button or anchor. Further, the benefits of the fixation device according to embodiments of the invention include a protective chamber for the tension element as it passes through organic tissue. In one or more embodiments, utilizing the fixation device allows a surgeon to secure complex off-axis tension elements at any depth and angle within bones or other tissue. Further, in one or more embodiments, utilizing the fixation device offers an eased ability to retrieve and adjust a suture as it is anchored by a surgical button on an outer surface of organic tissue.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. An orthopedic implant system, comprising:
a cannula including a body, a proximal end, a distal end opposite the proximal end, an inner surface, and an outer surface; the body sized and configured for insertion within a first bone tunnel having a first axis in a first bone, the body defining a passage that extends from the proximal end to the distal end, the proximal end having a button reception portion and a drive portion, the outer surface having a threaded portion extending radially from the body;
a button including a top end surface, a bottom end surface, and a circumferential outer surface, wherein the button defines a first aperture that extends from the top end surface to the bottom end surface and a second aperture that extends from the top end surface to the bottom end surface; the button configured and arranged to be removable affixed to the button reception portion of the cannula;
a suture anchor configured and arranged to engage a second bone including a second bone tunnel having a second axis, wherein the first axis is independent of the second axis; and
a suture configured and arranged to loop through the passage, the distal end, the second bone tunnel; wherein the suture is coupled to the suture anchor and tensionable through the first aperture and the second aperture of the button.

2. The system of claim 1, wherein the outer surface is symmetric about the first axis.

3. The system of claim 1, wherein the drive portion is a hexagonal feature on the inner surface.

4. The system of claim 1, wherein the proximal end is configured to rest at or below a top surface of bone.

5. The system of claim 4, wherein the top end surface is configured to rest at or below the top surface of bone.

6. The system of claim 1, wherein the passage is substantially collinear with the first axis.

7. The system of claim 1, wherein the suture is configured to be looped through the passage and a third bone tunnel along a third axis, to couple a second suture anchor and the button.

8. The system of claim 1, wherein the suture anchor is a second cannula and a second button.

9. The system of claim 1, wherein the suture is threaded through the first aperture and the second aperture from the bottom end surface to the top end surface of the button, wherein the suture is tightened at the top end surface.

10. The system of claim 1, wherein the top end surface and the bottom end surface of the button are flat.

11. The system of claim 1, wherein the circumferential outer surface of the button is threaded; wherein the button reception portion is threaded; wherein screwing the button within the button reception portion adjusts the height of the button with respect to the cannula; and wherein increasing the height of the button with respect to the cannula increases tension in the suture.

12. A surgical method, comprising:

forming a primary bone tunnel in a first bone along a first axis;

forming a secondary bone tunnel in a second bone along a second axis, wherein the second axis is independent from the first axis, wherein a suture anchor engages the second bone;

selecting a cannula including a body, a proximal end, a distal end opposite the proximal end, an inner surface, and an outer surface; the body sized and configured for insertion within the first bone tunnel, the body defining a passage that extends from the proximal end to the distal end, the proximal end having a button reception portion and a drive portion, the outer surface having a threaded portion extending radially from the body;

inserting the cannula within the primary bone tunnel;

providing a button at the button reception portion, the button including a top end surface, a bottom end surface, and a circumferential outer surface, wherein the button defines a first aperture that extends from the top end surface to the bottom end surface and a second aperture that extends from the top end surface to the bottom end surface; the button configured and arranged to be removable affixed to the button reception portion of the cannula;

looping the suture through the passage, the distal end, the second bone tunnel;

coupling the suture to the suture anchor; and tensioning the suture through the first aperture and the second aperture of the button.

13. A method, as in claim 12, further comprising inserting the cannula to rest at or below a top surface of bone.

14. A method, as in claim 13, further comprising inserting the button to rest at or below the top surface of bone.

15. A method, as in claim 12, further comprising passing the suture through a tissue graft.

16. A method, as in claim 12, wherein the suture anchor is a second cannula and a second button.

17. A method, as in claim 12, further comprising fixedly securing the suture to the button, the button to the button to the reception portion, and the suture to the suture anchor without tying any knots.

18. A method, as in claim 12, comprising fixedly securing a second anchor to said suture through a third bone tunnel having a third axis.

* * * * *